United States Patent [19]
Grossan

[11] 3,993,053
[45] Nov. 23, 1976

[54] PULSATING MASSAGE SYSTEM

[76] Inventor: Murray Grossan, 8930 Sepulveda Blvd., Los Angeles, Calif. 90045

[22] Filed: Aug. 5, 1975

[21] Appl. No.: 601,927

Related U.S. Application Data

[63] Continuation of Ser. No. 494,852, Aug. 5, 1974, abandoned.

[52] U.S. Cl. .................................. 128/64; 128/24.1
[51] Int. Cl.² ..................... A61H 7/00; A61H 29/00
[58] Field of Search ............. 128/64, 60, 24 R, 24.2, 128/DIG. 15, DIG. 20, 400, 402, 24.1

[56] References Cited
UNITED STATES PATENTS

| | | | |
|---|---|---|---|
| 2,930,594 | 3/1960 | MacCracken | 128/400 X |
| 3,288,132 | 11/1966 | Meredith | 128/64 X |
| 3,654,919 | 4/1972 | Birtwell | 128/64 |
| 3,670,723 | 6/1972 | Simjian | 128/64 |

*Primary Examiner*—Lawrence W. Trapp
*Attorney, Agent, or Firm*—Poms, Smith, Lande & Glenny

[57] ABSTRACT

A massaging system for application to the body for simulating muscular contraction in enhancing flow of venous blood and lymphatic fluid. The system includes a flexible pad having fixed to one face thereof a set of elastic tubing coil portions forming part of a recirculating hydraulic system including a pump for creating pulsating fluid flow. The segments of elastic tubing between the tubing portions fixed to the pad are disposed in substantially parallel relation, spaced from the fixed portions, and are supplied to a part of the body to be treated so that pulsations of fluid flow in the elastic segments are directed cardiocipetally, i.e. toward the heart. Thus the pulsations are transmitted through the wall of the elastic tubing segments and through the patient's skin and adjacent tissue, and are applied to the muscle. The cardiocipetal orientation of the tubing segments and of the resulting pressure pulsations longitudinally of the effected muscle serve to provide the pumping action in the adjacent veins and lymphatic passages which would normally be provided by muscular contractions during ordinary body movements. The pump of the system desirably includes means for controlling the pressure, the frequency of pulsations and the temperature of the circulating liquid, typically water. The size and shape of the pads, and the number of effective segments of elastic tubing applied to the skin, may be varied as desired to be adapted for use on virtually any area of the body.

3 Claims, 8 Drawing Figures

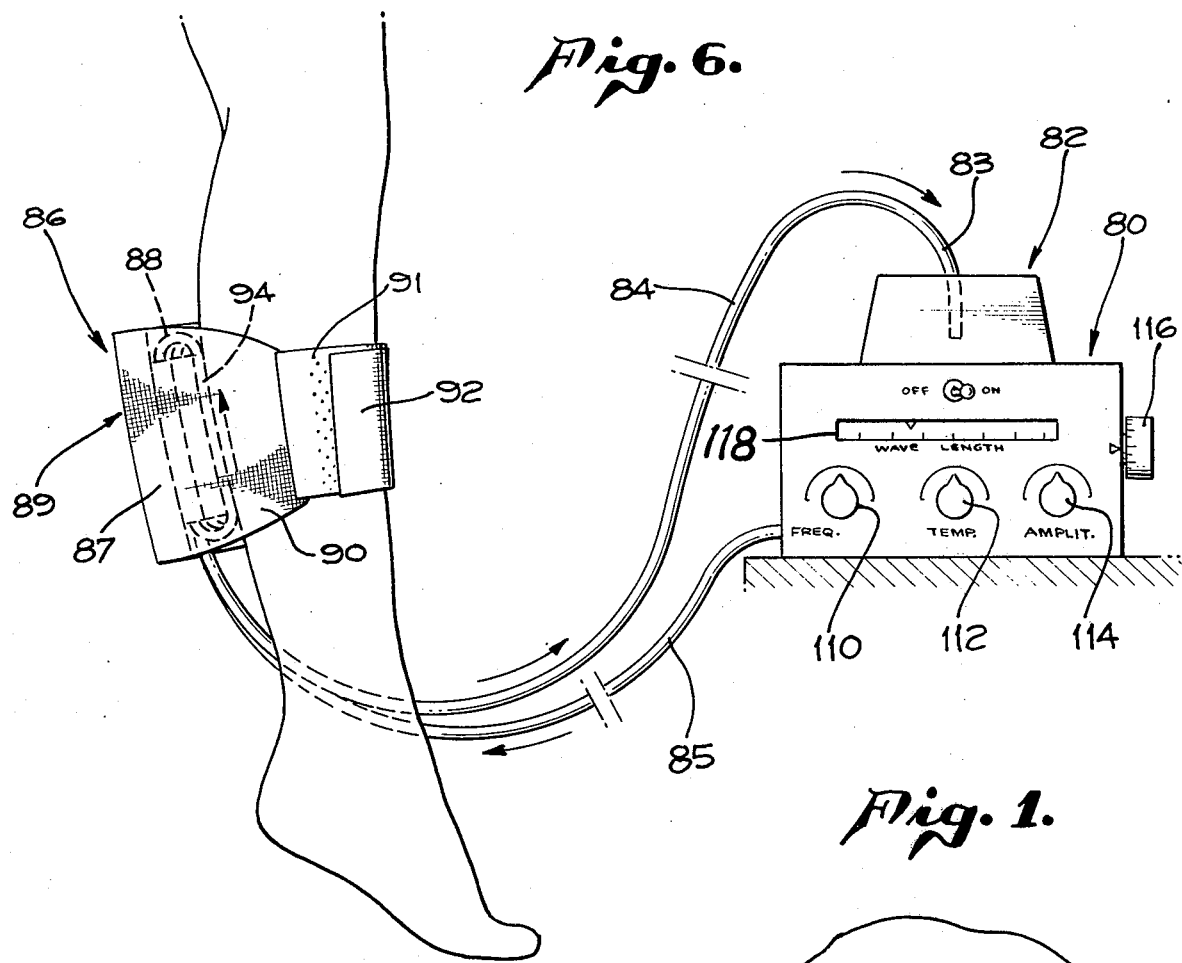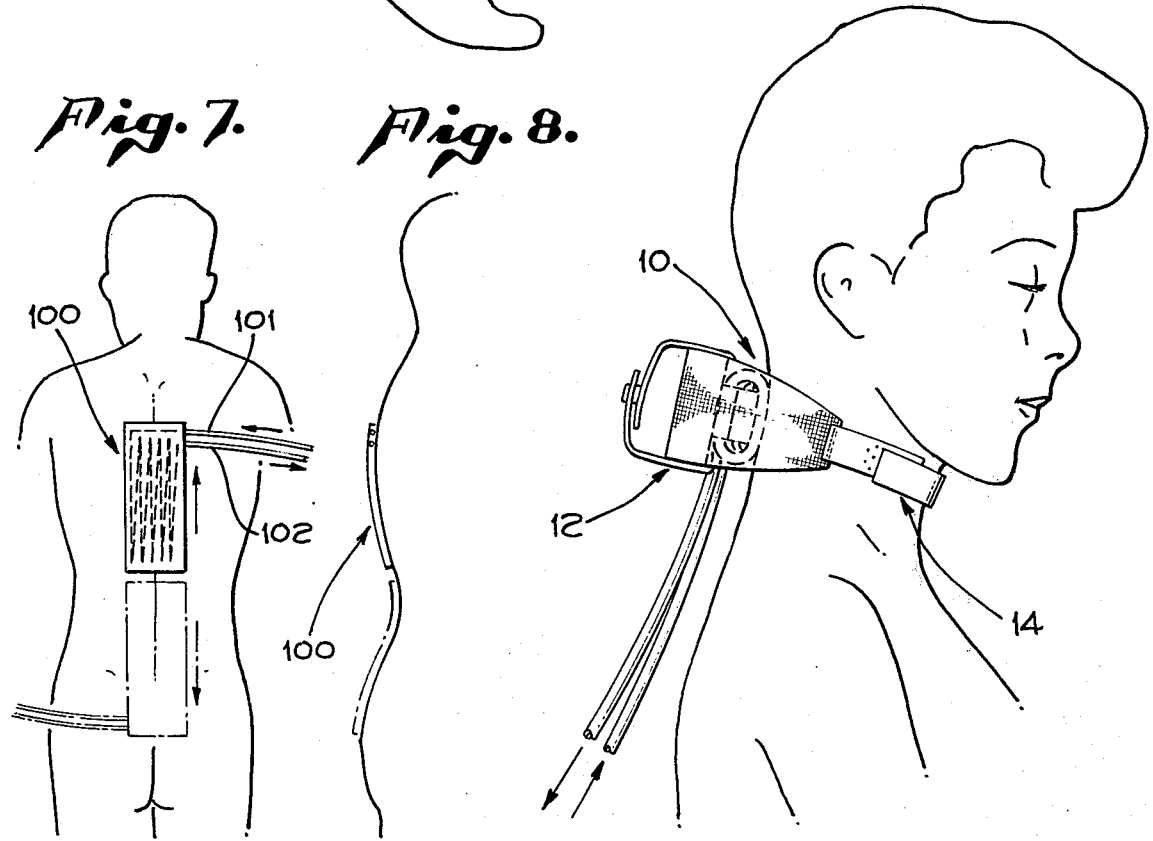

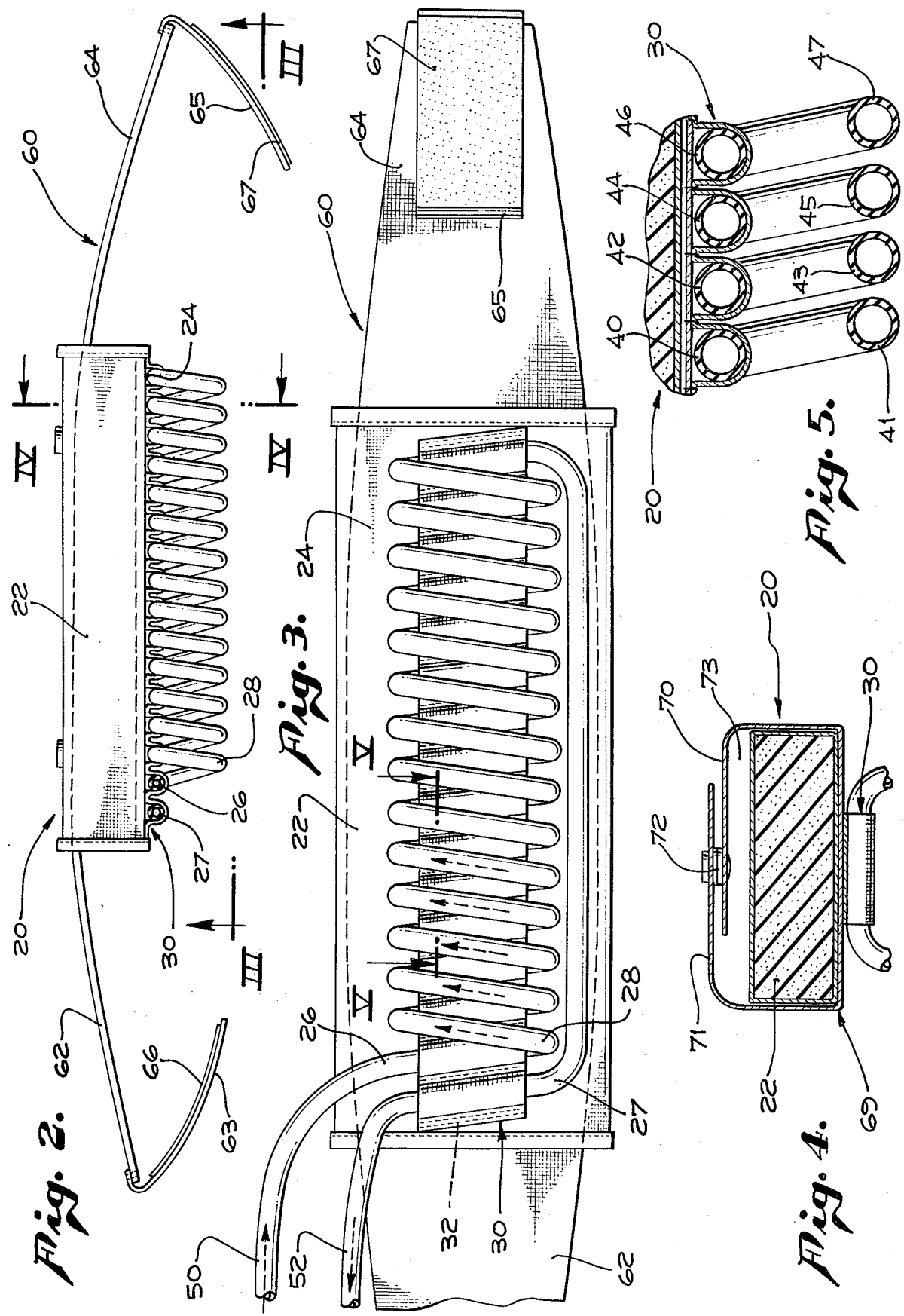

PULSATING MASSAGE SYSTEM

This is a continuation of abandoned application Ser. No. 494,852, filed Aug. 5, 1974.

BACKGROUND AND FIELD OF THE INVENTION

The present invention relates generally to a massaging system and method for application to the human body, and more particularly to a flexible massaging pad or similar structure provided on one face with a plurality of elongated segments or sections of elastic tubing which form part of a recirculating system for pulsating water flow in the tubing. In use, the pad is applied to the body so that the elastic tubing segments contact the skin of the body member to be treated in such a way that the pulsating water flow in the tubing is directed cardiocipetally, i.e. toward the heart. Moreover, the system includes means whereby the frequency of pulsation may be controlled by the user to an optimum value for a particular muscle, depending primarily upon the length of the muscle being treated. The system also includes means for controlling the temperature of the water or equivalent liquid circulated in the tubing, as well as means for controlling the amplitude or strength of the pressure pulsations imparted to the liquid in the system. Because of the cardiocipetal direction of the pulsations in the elastic tubing transmitted to adjacent muscles, use of the system substantially enhances the flow of venous blood and lymphatic fluid. The system thus serves in effect as a substitute for the beneficial results of exercise such as walking, in maintaining good flow of venous blood and lymphatic fluid by applying rhythmic impulses tending to simulate contraction of the muscle or muscles adjacent to the portion of the body to which the device is applied, thus providing the benefits of isometric exercise of those muscles.

The advantages of physiotherapy in either causing or simulating muscular contraction have been long recognized, particularly in the treatment of patients who are not ambulatory, as well as in other situations where stimulation of the circulation is desirable in order to minimize lymphatic edema, loss of calcium, possible formation of blood clots and the like. Electrical stimulation of the affected muscles has been done under certain circumstances, but such treatment is relatively painful to the patient, and requires special and comparatively expensive equipment, as well as specialized training of the person applying the treatment. Other therapeutic techniques in past and present use include manual massage, hydro-massage as by a bath of agitated water, mechanical vibrators and heating pads. Each of these techniques and systems, although intended to accomplish the purpose of enhancing flow of venous blood and lymphatic fluid, nevertheless have certain disadvantages, both in terms of cost and in terms of effectiveness. The device and system of the present invention constitute an improvement over the systems heretofore and presently in use in a number of important respects, as will be described in detail hereinafter.

It is accordingly a principal purpose of the present invention to provide and disclose a novel system and device for enhancing the flow of venous blood and lymphatic fluid. Additional objects and purposes are to provide, in such a device and system, means including a plurality of parallel adjacent tubing sections for applying to adjacent muscles of the body rhythmic unidirectional pulsations in a cardiocipetal direction; to provide such a device and system of simplified construction whereby it can be effectively used by the patient himself, after a very short period of professional instruction; to provide such a system and device which is inexpensive to manufacture and use; and for other objects and purposes as will be understood from the following description of preferred embodiments of the invention, taken in connections the accompanying drawings.

BRIEF DESCRIPTION OF THE DRAWINGS

FIG. 1 is a fragmentary right side view of a patient's head, neck and upper torso, showing one form of the present device applied to the back of the patient's neck.

FIG. 2 is a side elevational view of a somewhat larger form of massaging pad in accordance with the present invention, shown in extended condition and provided with attachment flaps or tabs at opposite ends of the pad.

FIG. 3 is an elevational view taken on the arrows III—III of FIG. 2.

FIG. 4 is a fragmentary sectional view taken on the arrows IV—IV of FIG. 2.

FIG. 5 is a fragmentary sectional view taken on the arrows V—V of FIG. 3.

FIG. 6 is an overall view showing a typical form of the pumping device in accordance with the present invention, operatively connected through tubing to the massage pad of the present invention applied to the calf of a patient's leg.

FIG. 7 is a partial rear view of a patient, with, in solid lines, a pad in accordance with the present invention applied to the upper central portion of the patient's back and, in dotted outline, the same or a similar pad applied to the lower portion of his back.

FIG. 8 is a fragmentary side view of the assembly of FIG. 7.

DETAILED DESCRIPTION

Referring now in detail to the drawings, there is indicated generally at 10 in FIG. 1 the neck of a patient being treated in accordance with the present invention. A massaging pad indicated generally at 12 includes means for temporary attachment to the neck of the patient, such means being indicated generally at 14 and desirably consisting of a pair of straps or tabs having mutually engaging adhesive-like surfaces for selective attachment to and detachment from the portion of the body being treated.

As best seen in FIG. 2, showing a somewhat larger form of massaging pad assembly indicated generally at 20, the assembly includes a soft, flexible backing member 22 which may consist, for example, of sponge rubber or rubber substitute, to permit the pad assembly to adapt itself to the contour of the portion of the body being treated. The front face 24 of pad 22 has affixed thereto the rear portions of a succession of coils of hollow flexible tubing, as well as inlet and outlet portions 26 and 27 of the tubing, the latter being shown in section. These tubing portions are retained on the front face 24 of the pad by means here shown as including a flexible strip indicated generally at 30 of fabric material or the like, which is attached as by stitching 32 to the front face 24 of the pad, along lines between successive tubing portions.

The front portions of the tubing, or lower portions as seen in FIG. 2, constitute the operational sections of the tubing in accordance with the present invention. As seen in FIG. 3, the first operational tubing section is indicated at 28 and, as indicated by the upwardly directed arrow on section 28 and several successive operational sections, the flow of liquid in the operational tubing sections is upwardly as there seen.

The construction will be more clearly seen by reference to the sectional view of FIG. 5. Thus in FIG. 5 successive rear coil portions which are attached by means 30 to pad 20 are indicated at 40, 42, 44 and 46, with the corresponding front portions or sections of the tubing being indicated at 41, 43, 45 and 47.

With further reference to FIG. 3, the inlet portion 26 of the tubing is formed integrally with inlet conduit 50, which is adapted to receive pulsating flow of water or other liquid from pump means to be later described, and the outlet portion 27 of the tubing is formed integrally with conduit 52, which serves as a return to the pump means to form a recirculating system. As previously mentioned, during actual application and use of the present device, the massaging pad assembly is applied to the body member in such a way that the direction of pulsating flow indicated by the arrows on the front tubing portions of FIG. 3 is cardiocipetal.

In the form of the invention shown in FIGS. 2 and 3, the strap means for maintaining the present device in proper contact with the patient's body may include a base strap indicated generally at 60 attached as by stitching to the rear face of pad 20 and having a length substantially greater than the length of the pad, thereby providing strap extensions 62 and 64 projecting beyond opposite ends of the pad. At the outermost ends of the extensions 62 and 64 there are provided attachment tabs 63 and 65 respectively. In the present illustrative form of the invention, tabs 63 and 65 may be provided with interengageable mating hook and loop adhesive means such as the material sold under the trademark "Velcro." Thus the upper face of tab 63 as seen in FIG. 2 may be provided with a layer of that material indicated at 66, and the lower face of tab 65 may be provided with a mateable layer 67 of the material.

In addition to the attachment means just described, there may also be provided in accordance with the invention strap means for receiving the hand of a person, either the patient himself or another person supervising the treatment. Such means are best seen in FIG. 4, and include a strap indicated generally at 69 having inner and outer extension flaps 70 and 71 respectively, provided with one or more snap attachment means 72. The flaps 70 and 71 are attached to the massage pad 20 as by stitching or equivalent means, and are so sized as to provide sufficient space 73 immediately adjacent to the rear or outer surface of the pad, within which a person may insert his hand during handling and application of the present device.

In FIG. 6 there is shown a complete system in accordance with the present invention, with the massage pad being applied to the calf of a patient. More particularly, a pump unit is indicated generally at 80, and may resemble in important characteristics that shown in U.S. Pat. No. 3,227,158. Operation in accordance with the present invention contemplates recirculation of the water being pumped by unit 80, and for this purpose there is provided an upper reservoir or tank indicated generally at 82, into which the outlet end portion 83 of the return conduit tubing 84 is placed. An outlet conduit tubing 85 extends leftwardly as seen in FIG. 6 from pump unit 80. Both conduit tubings 84 and 85 extend to the massage pad assembly indicated generally at 86, the conduit tubings being connected to, and preferably formed integrally with, the tubing of assembly 86. That assembly is similar in major respects to the massage pad assembly 20 heretofore described in connection with FIGS. 2–5 inclusive except that the tubing therein may include a smaller number of coils than the somewhat larger massage pad assembly 20 of FIG. 2. Thus assembly 86 includes a backing pad 87 having attached thereto the coiled tubing 88 seen in dotted outline in FIG. 6, in substantially the same manner as heretofore described in connection with the form of the invention shown in FIG. 2. Similarly, pad assembly 86 is provided with attachment means, desirably including a backing strap indicated generally at 89, which includes a pair of oppositely extending strap extensions, one of which is seen at 90, which has attached thereto an attachment tab 91, similar to the attachment tab 63, and adapted to detachably mate with attachment tab 92, which in turn is attached to the opposite strap extension, concealed from view in FIG. 6.

With continuing reference to FIG. 6, it will be seen that liquid such as water will be supplied under pulsating pressure in outlet conduit tubing 85 from pump 80 to the coiled tubing 88 within the massage pad assembly 86, and more particularly to the front operational tubing portions adjacent to the skin of the patient, one such portion being seen in phantom and indicated at 94. The flow of liquid is again cardiocipetal, or upwardly as seen in FIG. 6, as indicated by the arrow adjacent to tubing portion 94.

FIGS. 7 and 8 show the application of a massage pad assembly of the present invention to the back of a patient, either in the upper back portion as shown in solid lines or in the lower back portion as shown in dotted outline. Thus a massage pad assembly indicated generally at 100 includes coiled tubing connected to inlet tubing conduit 101 and outlet tubing conduit 102, and the front operational tubing portions which are adjacent to the patient's skin carry liquid whose pulsating flow is cardiocipetal, as indicated by the upwardly directed arrow adjacent to pad assembly 100. For massage of the lower back pad assembly is turned upside down into the position shown in dotted outline, the flow of liquid in the tubing portions adjacent to the skin again being cardiocipetal, or downwardly as indicated by the phantom arrow.

With further reference to FIG. 6, pump unit 80 is provided with manually operable dials for controlling the temperature of the pumped water, the frequency and amplitude of the pulsations, and the time duration of a particular treatment. Additionally, an indicator of wave length may be provided, in order most effectively to apply pulsations to particular areas of the body. Thus, the unit 80 includes a frequency control dial 110, a temperature control dial 112, an amplitude control dial 114, and a timing control dial 116. An elongated wave length indicator 118 gives a showing inversely proportional to the frequency, and may be calibrated to assist the user in adjusting the frequency to be best adapted for treatment of specific muscular areas; generally the longer the muscle, the longer should be the wave length of pulsating liquid flow provided by pump unit 80. The temperature of the liquid flow may typically be that of the body or a little higher, e.g. 100° to 110° F. Under some circumstances advantageous results may be obtained with substantially higher or lower temperatures, depending upon a number of factors including patient preference, empirical determination of effectiveness on certain body members and the like. A typical treatment may last for 15 to 20 minutes, and timing control dial 116 may be set as desired for this purpose.

Enhanced circulation resulting from the use of the method and system of the present invention is helpful in tending to alleviate muscle spasm and rigidity, particularly in the case of inactive muscles as in whiplash injuries to the neck and back or non-ambulatory patients. When applied to the abdominal area, the enhanced circulation tends to remove adipose tissue, and when applied to the neck as shown in FIG. 1, the resulting soothing increase in circulation tends to induce sleep. In addition to the body areas above mentioned and illustrated, pads may be especially formed for application to the thigh, the facial area and the upper arm. The latter is particularly advantageous following mastectomy. It will be seen that the present invention, being independent of the direction of gravity, is inherently advantageous over hydro massage procedures where the affected body part or member must be submerged in water for treatment, which is impractical where the patient is in a body cast, and in many other situations.

I claim:
1. A system for enhancing flow of venous blood and lymphatic fluid comprising:
    a set of tubing segments arranged in parallel generally adjacent relation, said tubing segments being successive corresponding parts of a coil;
    applicator means for maintaining said set in contact with a patient's skin, with the tubing segments generally parallel with venous flow in the adjacent body member;
    and means for forcing pulsating fluid through said tubing segments in a cardiocipetal direction.
2. The invention as defined in claim 1 wherein said applicator means comprises a flexible pad of resilient material.
3. The invention as defined in claim 2 wherein coil portions other than said segments are attached to the applicator means.

* * * * *